US009572629B1

(12) United States Patent  
Papac et al.

(10) Patent No.: US 9,572,629 B1  
(45) Date of Patent: Feb. 21, 2017

(54) SUB-MICRON ALIGNMENT OF A MONITORING FIBER FOR OPTICAL FEEDBACK IN AN OPHTHALMIC ENDO-ILLUMINATION SYSTEM

(71) Applicant: NOVARTIS AG, Basel (CH)

(72) Inventors: Michael J. Papac, North Tustin, CA (US); Vit Ulinskas, Tustin, CA (US)

(73) Assignee: Novartis AG, Basel (CH)

( * ) Notice: Subject to any disclaimer, the term of this patent is extended or adjusted under 35 U.S.C. 154(b) by 3 days.

(21) Appl. No.: 14/840,349

(22) Filed: Aug. 31, 2015

(51) Int. Cl.
*A61B 3/10* (2006.01)
*F21V 8/00* (2006.01)
*G02B 6/42* (2006.01)

(52) U.S. Cl.
CPC .................. *A61B 90/30* (2016.02); *A61B 3/10* (2013.01); *G02B 6/0006* (2013.01); *G02B 6/4231* (2013.01); *G02B 6/4239* (2013.01); *A61B 2090/306* (2016.02)

(58) Field of Classification Search
USPC ........................................................ 351/221
See application file for complete search history.

(56) References Cited

U.S. PATENT DOCUMENTS

| 5,039,191 | A  | 8/1991  | Myszka            |
| 5,463,710 | A  | 10/1995 | Filgas et al.     |
| 5,815,626 | A  | 9/1998  | Kuba et al.       |
| 5,999,255 | A  | 12/1999 | Dupee et al.      |
| 7,292,323 | B2 | 11/2007 | Artsyukhovich et al. |
| 8,371,695 | B2 | 2/2013  | Papac et al.      |
| 8,474,977 | B2 | 7/2013  | Hahn et al.       |
| 8,542,962 | B2 | 9/2013  | Smith et al.      |
| 8,561,280 | B2 | 10/2013 | Diao et al.       |
| 8,662,670 | B2 | 3/2014  | Papac et al.      |
| 9,107,730 | B2 | 8/2015  | Huculak et al.    |
| 2001/0055462 | A1 | 12/2001 | Seibel         |
| 2002/0028049 | A1 | 3/2002  | Bartur et al.  |
| 2003/0147601 | A1 | 8/2003  | Bartur et al.  |

(Continued)

FOREIGN PATENT DOCUMENTS

| EP | 1265087 A2 | 12/2002 |
| EP | 1949877 B1 | 6/2012  |

(Continued)

OTHER PUBLICATIONS

PCT/IB2016/052513; International Search Report, International Searching Authority, Jul. 11, 2016, 4 pgs.

*Primary Examiner* — Jack Dinh

(57) ABSTRACT

An ophthalmic endo-illumination system includes a light source producing a light beam, a beam splitter configured to split the light beam into a first beam provided to a fiber port and a second beam coupled to a monitoring fiber, and an alignment system for aligning the monitoring fiber. The alignment system includes a moveable ferrule housing having the monitoring fiber secured therein and a displacement mechanism for displacing housing in a first direction. The displacement mechanism includes a transfer spring coupled to the housing and a screw actuator having a sloped surface contacting a motion transfer ball such that movement of the screw actuator causes the motion transfer ball to move along the sloped surface, the motion transfer ball contacting the transfer spring such that movement of the motion transfer ball along the sloped surface causes a displacement of the transfer spring, thereby displacing the housing in the first direction.

20 Claims, 5 Drawing Sheets

(56) References Cited

U.S. PATENT DOCUMENTS

| | | |
|---|---|---|
| 2008/0183160 A1 | 7/2008 | Papac et al. |
| 2008/0269728 A1 | 10/2008 | Buczek et al. |
| 2008/0291432 A1 | 11/2008 | Horvath et al. |
| 2011/0292344 A1 | 12/2011 | Papac et al. |
| 2012/0203075 A1 | 8/2012 | Horvath et al. |
| 2015/0366432 A1 | 12/2015 | Artsyukhovich et al. |

FOREIGN PATENT DOCUMENTS

| | | |
|---|---|---|
| WO | 99/63370 A2 | 12/1999 |
| WO | 2014/145465 A2 | 9/2014 |
| WO | 2014/182212 A1 | 11/2014 |
| WO | 2016032797 A1 | 3/2016 |
| WO | 2016100082 A1 | 6/2016 |

SUB-MICRON ALIGNMENT OF A MONITORING FIBER FOR OPTICAL FEEDBACK IN AN OPHTHALMIC ENDO-ILLUMINATION SYSTEM

RELATED APPLICATIONS

This present disclosure is related to U.S. patent application Ser. No. 14/468,696 filed Aug. 26, 2014, the entire contents of which is hereby incorporated by reference.

FIELD

This present disclosure relates generally to the ophthalmic illumination and, more particularly, to sub-micron alignment of a monitoring fiber for optical feedback in an ophthalmic endo-illumination system.

BACKGROUND

An ophthalmic endo-illumination probe may be used to provide illumination in an ophthalmic surgery. In particular, an ophthalmic endo-illumination probe may be inserted into an eye to provide illumination inside the eye during an ophthalmic surgery. The ophthalmic endo-illumination probe may be connected to an optical port of an ophthalmic endo-illumination system. The ophthalmic endo-illumination system may include a light source that produces light and a condenser that couples the light into the optical fiber of the ophthalmic endo-illumination probe when the endo-illumination probe is connected to the optical port.

During the assembly of the ophthalmic endo-illumination system, the position and tilt of the light beam from the condenser may be adjusted relative to the optical port to achieve a desired coupling efficiency of the light beam into an ophthalmic endo-illumination probe connected at the optical port. Then, the assembly of the optical port may be fixed to maintain the coupling position and the coupling efficiency of the light beam into an ophthalmic endo-illumination probe when connected to the optical port. Despite fixation at the assembly stage, various factors may cause movement of one or more components of the system, which may result in a decrease in the coupling efficiency achieved at the fiber port. Such factors may include shock and vibration imparted to the optical port assembly during shipment and setup, thermal-induced expansion, rotation and distortion of opto-mechanical mounts used to direct the light beam, thermal-induced motion of the optical fiber port, or beam motion caused by movement of adjustable reflective elements within the system, such as a rotatable or translatable variable beam splitters.

SUMMARY

The present disclosure concerns the monitoring of a coupling efficiency at a fiber port of an ophthalmic endo-illumination system such that a desired coupling efficiency may be maintained. More particularly, the present disclose relates to sub-micron alignment of a monitoring fiber in an ophthalmic endo-illumination system, the monitoring fiber providing optical feedback in order to facilitate the maintenance of a desired coupling efficiency at the fiber port of the ophthalmic endo-illumination system.

In certain embodiments, an ophthalmic endo-illumination system includes a light source producing a light beam, a beam splitter disposed between a fiber port and a condenser that is configured to split the light beam into a first beam provided to the fiber port and a second beam coupled to a monitoring fiber, and an alignment system for aligning the monitoring fiber with the second beam. The alignment system includes a moveable ferrule housing having the monitoring fiber secured therein and a first displacement mechanism for displacing the moveable ferrule housing in a first direction. The first displacement mechanism includes a transfer spring coupled to the moveable ferrule housing and a screw actuator having a sloped surface contacting a motion transfer ball such that movement of the screw actuator causes the motion transfer ball to move along the sloped surface, the motion transfer ball contacting the transfer spring such that movement of the motion transfer ball along the sloped surface causes a displacement of the transfer spring, thereby displacing the moveable ferrule housing in the first direction.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
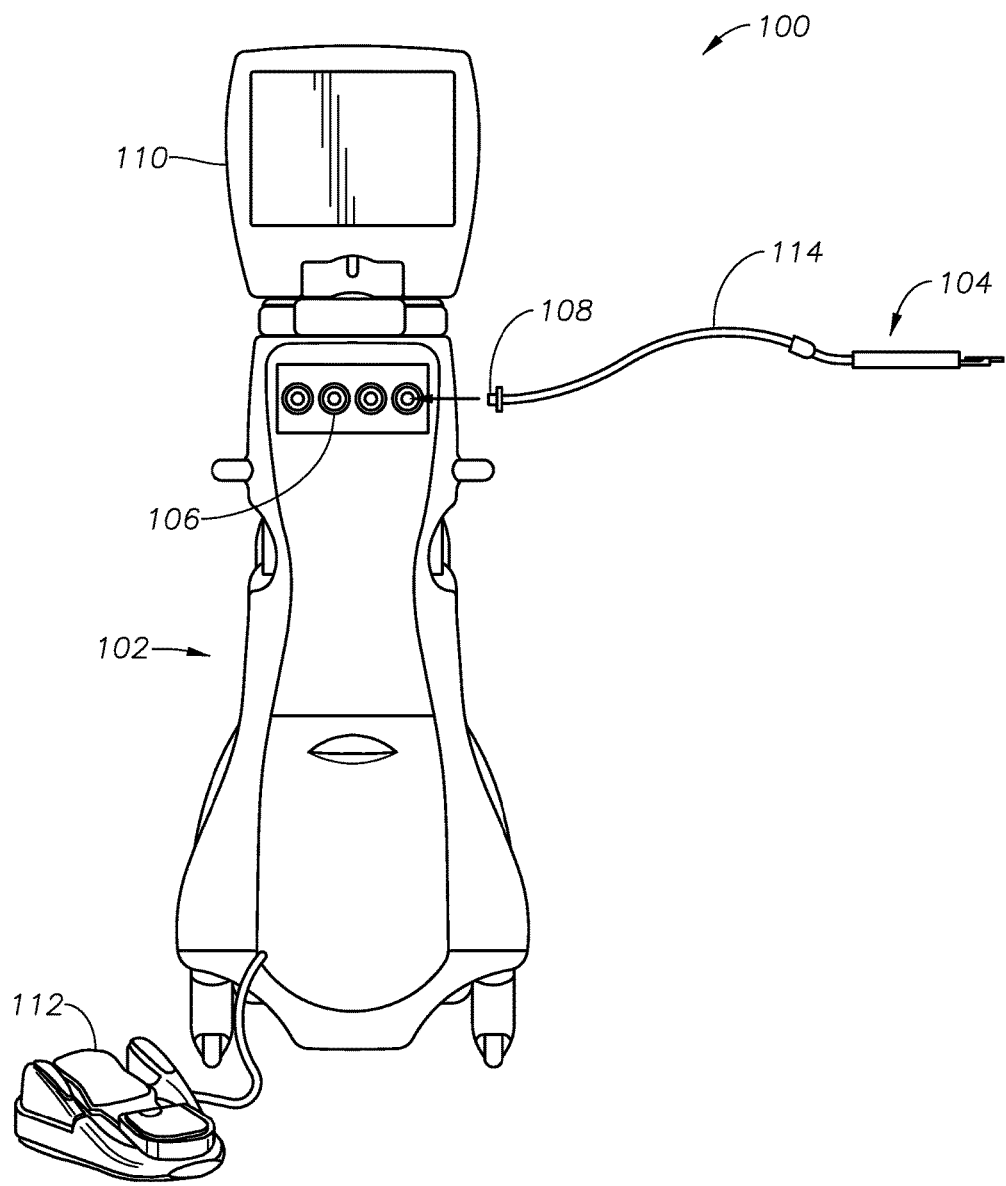
FIG. 1 illustrates an example surgical system, according to certain embodiments of the present disclosure.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure relates to an ophthalmic endo-illumination system comprising a monitoring fiber for providing feedback regarding the optical coupling efficiency of a light beam into an ophthalmic fiber probe (e.g., using an optical sensor coupled to the monitoring fiber to detect an amount of light output from the monitoring fiber). The ophthalmic endo-illumination system may include a condenser that is configured to couple a light beam into a proximal end of the ophthalmic fiber probe connected to a fiber port of the ophthalmic endo-illumination system. A beam splitter may be provided between the condenser and the fiber port to split the light beam into a first beam which is coupled into the ophthalmic fiber probe and a second beam which is coupled into the monitoring fiber. Because accuracy of the feedback provided by the monitoring fiber may be dependent on accurate alignment of the monitoring fiber relative to the condenser and beam splitter, certain embodiments of the present disclosure may provide an alignment system facilitating sub-micron alignment of the monitoring fiber.

FIG. 1 illustrates an example surgical system 100, according to certain embodiments of the present disclosure. Surgical system 100 may include a surgical utility supplying device 102 with an associated display screen 110 showing data relating to system operation and performance during a surgical procedure. Surgical system 100 may further include a surgical implement 104 configured to be connected to the surgical utility supplying device 102 via a surgical utility connector 108 configured to interface with a utility port 106 of surgical utility supplying device 102. The surgical utility supplying device 102 may supply various surgical implements 104, such as surgical implements 104 for providing imaging light, illumination light, compressed air, vacuum, pressurized liquid, or any other suitable surgical implements 104. As just one example, utility port 106 may comprise a fiber port, surgical implement 104 may comprise an ophthalmic endo-illumination probe, and surgical utility supplying device 102 may supply visible light to the ophthalmic endo-illumination probe via the fiber port.

In certain embodiments, surgical utility supplying device 102 may include multiple utility ports 106 each corresponding to a particular type of surgical implement 104 for providing a certain type of utility. For example, surgical utility supplying device 102 may output (1) visible light to a fiber port configured to receive an ophthalmic fiber probe, and (2) compressed air to a compressed air port configured to receive a surgical vitrectomy probe. In certain embodiments, multiple utility ports 106 may support simultaneous use of a number of different types of surgical implements 104.

In certain embodiments, a surgical utility connector 108 configured to couple to a utility port 106 may be coupled via a cable 114 to a surgical implement 104, the cable 114 facilitating transmission of a utility to the surgical implement 104. For example, cable 114 may comprise a fiber optical cable (e.g., for transmitting visible light from surgical utility supplying device 102 to an ophthalmic endo-illumination probe), tubing (e.g., for transmitting one or more of compressed air, vacuum, and pressurized liquid from surgical utility supplying device 102 to a surgical vitrectomy probe), or any other suitable transmission device.

In certain embodiments, surgical system 100 may additionally include a foot pedal 112 connected to the surgical utility supplying device 102 for controlling the dispensing of a particular utility (e.g., imaging light, illumination light, compressed air, vacuum, pressurized liquid, or any other suitable utility) via a surgical implement 104. For example, a user may control the dispensing of the utility by selectively pressing and releasing the foot pedal 112.

Figure 2:
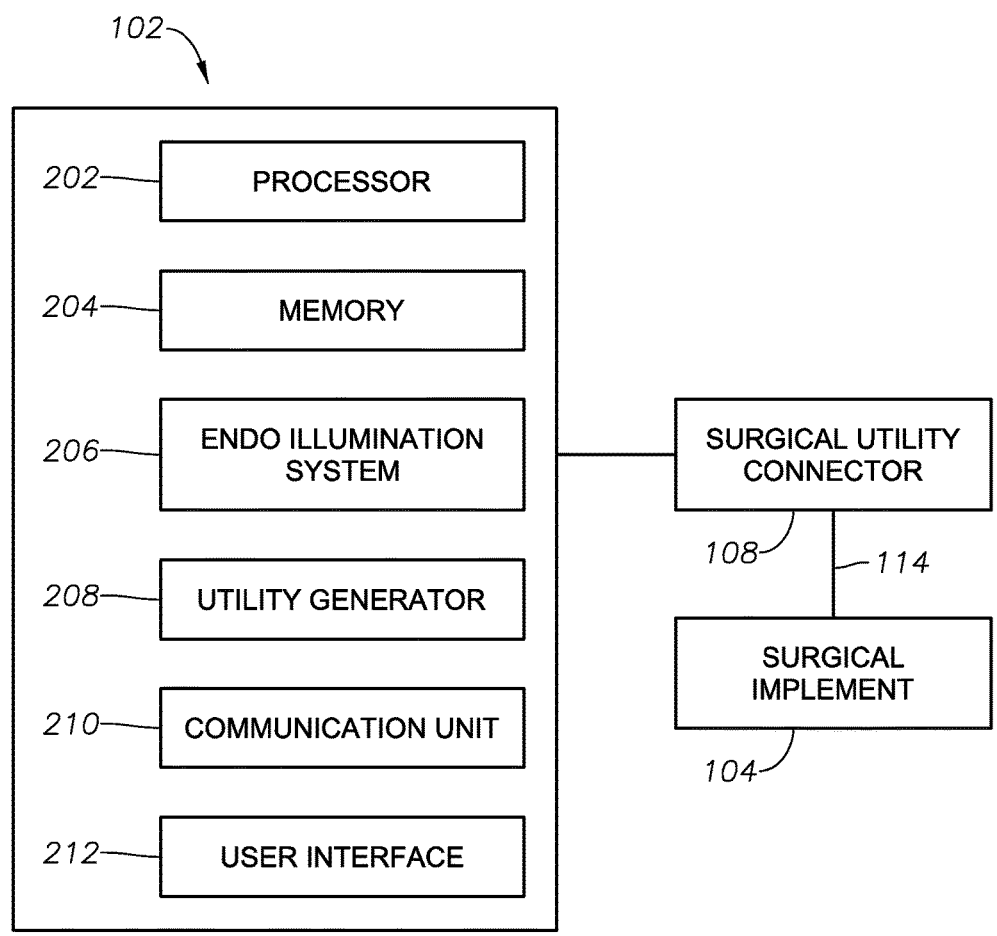
FIG. 2 illustrates a schematic diagram of the exemplary surgical utility supplying device of FIG. 1, according to certain embodiments of the present disclosure.

FIG. 2 illustrates a schematic diagram of exemplary surgical utility supplying device 102, according to certain embodiments of the present disclosure. The surgical utility supplying device 102 may include a processor 202 and memory 204. Processor 202 may be configured to perform calculation and determination for controlling various operations of the surgical utility supplying device 102. Processor 202 may receive various signal inputs and make various determinations based on the signal inputs. For example, the processor 202 may receive optical feedback signals from an optical sensor configured to detect an amount of a light output from a monitoring fiber to determine a coupling efficiency of a light beam into an optical fiber (as described in further detail below). Processor 202 also may control the display screen 110 to display various information regarding the operations of the surgical utility supplying device 102 to notify various information to the user. Memory 204 may be configured to store information permanently or temporarily for various operations of the surgical utility supplying device 102. For example, memory 204 may store programs that may be executed by the processor 202 to perform various functions of the surgical utility supplying device 102. Memory 204 also may store various data relating to operation history, user profile or preferences, various operation and surgical settings, and the like. Programs and information stored in the memory 204 may be continuously updated to provide customization and improvement in the operation of the surgical utility supplying device 102. In certain embodiments, memory 204 also may further include programs and information relating to operational parameters for coupling efficiency at different fiber ports.

In certain embodiments, surgical utility supplying device 102 may include an endo-illumination system 206. The endo-illumination system 206 may include optical components configured to couple a light beam into an ophthalmic fiber probe connected at a utility port (e.g., fiber port) of the surgical utility supplying device 102. As discussed in further detail below, the endo-illumination system 206 may include a collimator configured to receive light from a light source and collimate the light into a light beam, spectral filters configured to filter the light beam into desired spectrums, and a condenser configured to couple the light beam into an optical fiber of the ophthalmic fiber probe.

In certain embodiments, surgical utility supplying device 102 may include a utility generator 208. Utility generator 208 may include motors, light emitting devices, pumps, or any other suitable device for generating an appropriate utility. For example, utility generator 208 may include suitable device for generating illuminating light, imaging light, pressured liquid, compressed air, and the like. In certain embodiments, utility generator 208 may be connected to an external utility source to receive a utility externally. For example, utility generator 208 may be connected to a vacuum source or an air compressor to receive vacuum or compressed air, respectively. Utility generator 208 may supply various utilities to respective utility ports 106.

In certain embodiments, surgical utility supplying device 102 may include a communication unit 210. Communication unit 210 may include various communication devices, such as Ethernet card, wi-fi communication device, telephone device, digital I/O (Input-Output) ports or the like, that may allow the surgical utility supplying device to send and receive information to and from other devices. For example, communication unit 210 may receive input from other surgical devices to coordinate a surgical operation. In another example, communication unit 210 may transmit and receive messages or notifications, such as email, text, or other messages or notifications to a user's mobile device to notify certain information to the user.

In certain embodiments, surgical utility supplying device 102 may include a user interface 212. User interface 212 may include user input devices, such as a keyboard, a touch screen, the foot pedal 112, a mouse, a microphone, or the like that allow a user to input instructions to the surgical utility supplying device 102. For example, the user may enter parameters for a utility and operate the foot pedal 112 to dispense the utility to the surgical implement 104. The user interface 212 may additionally include user output devices, such as a display screen 110, an audio speaker, LED (light-emitting diode) lights, or other visual or tactile signals that convey information to a user. For example, an audio speaker may emit an alarm when a coupling efficiency at a particular fiber port drops below a certain threshold during a surgical operation. Thus, the user interface 212 may enable a user to interact with the surgical utility supplying device 102 during surgical operations.

Figure 3A:
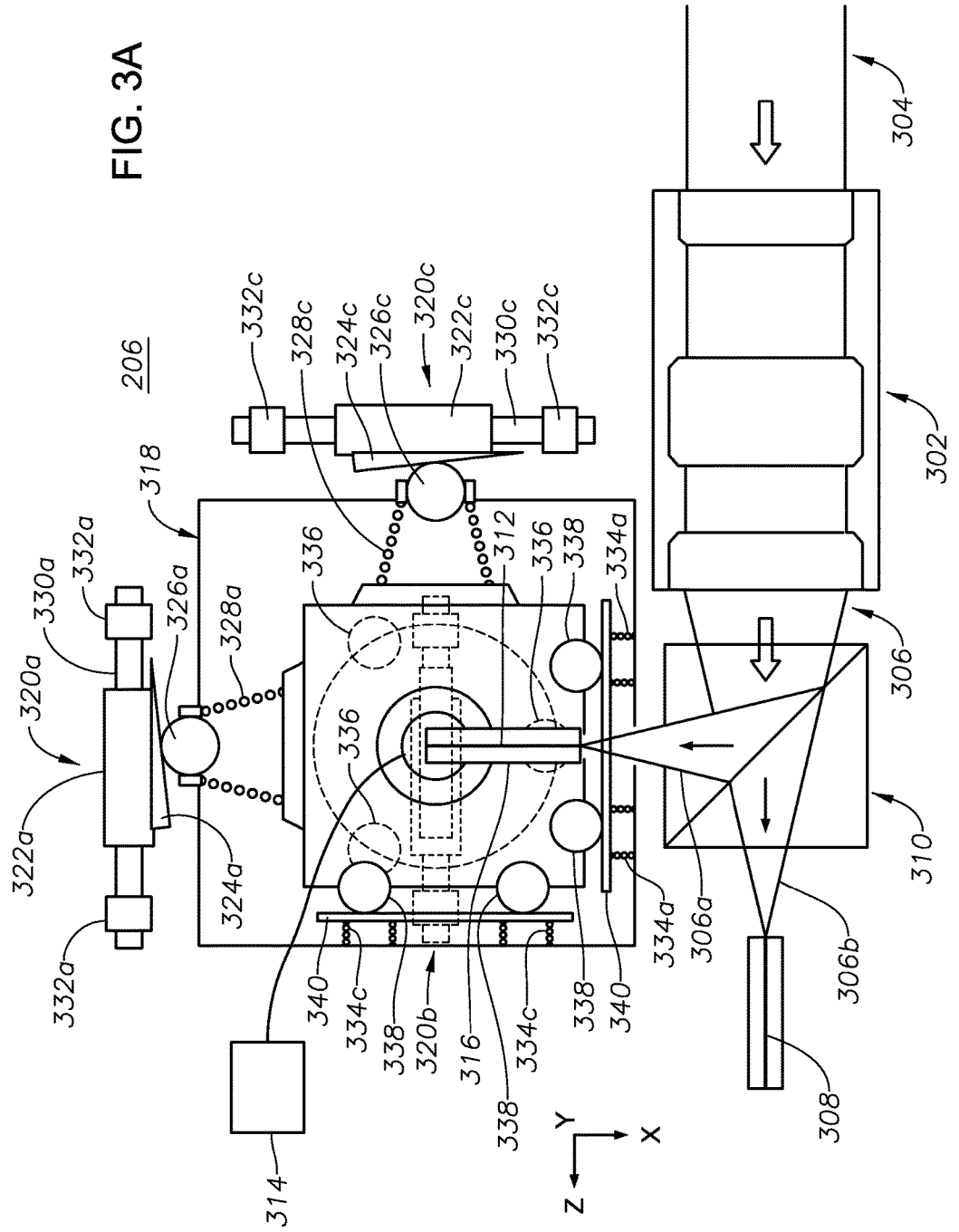
FIGS. 3A-3B illustrate a schematic diagram of the exemplary ophthalmic endo-illumination system of FIG. 2, according to certain embodiments of the present disclosure.
Figure 3B:
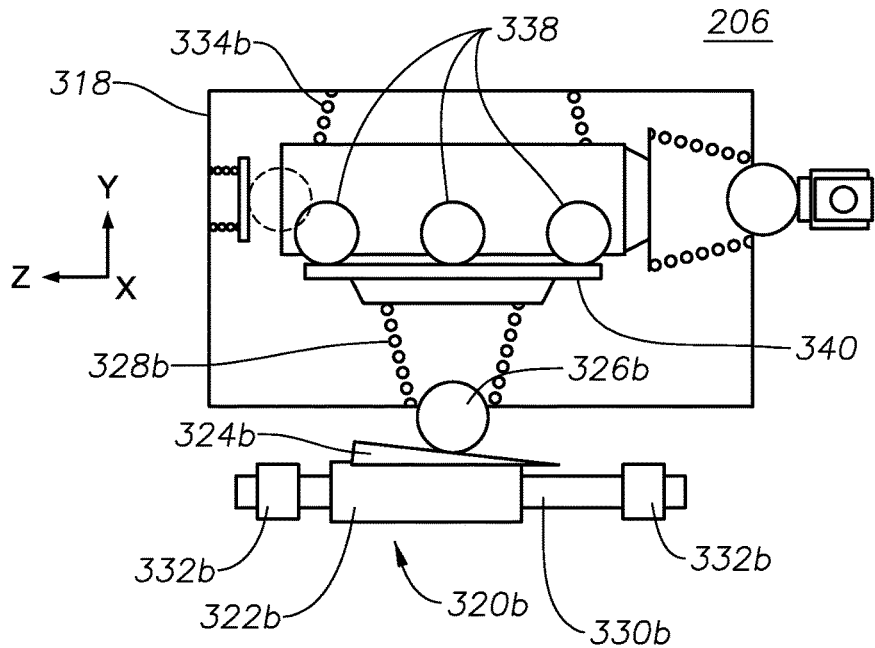

FIGS. 3A-3B illustrate a schematic diagram of an exemplary ophthalmic endo-illumination system 206, according to certain embodiments of the present disclosure. Ophthalmic endo-illumination system 206 may include a condenser 302 configured to receive a light beam 304. In particular, a light source (not shown in FIG. 3) may produce a light which may be collimated into a light beam 304 by a collimator (not shown). Condenser 302 may receive the light beam 304 and generate a condensed light beam 306 for coupling into an optical fiber 308 of a surgical implement 104 (e.g., an ophthalmic fiber probe) connected to the utility port 106 (e.g., a fiber port).

In certain embodiments, ophthalmic endo-illumination system 206 may include a beam splitter 310 disposed between condenser 302 and optical fiber 306. Beam splitter 308 may be configured to split the condensed light beam 306 into a first beam 306a and a second beam 306b. For example, beam splitter 304 may receive the condensed light beam 306 from condenser 302 and transmit a portion of the light beam (i.e., first beam 306a) while reflecting a portion of the light beam (i.e., second beam 306b). First beam 306a may continue on its path for coupling into to optical fiber 308, while second beam 306b may be diverted (e.g., in a direction perpendicular to first beam 306a) such that it may be coupled into a monitoring fiber 312.

Beam splitter 310 may be a beam splitter cube or any other optical device configured to receive a light beam and split the light beam into two different light beams. As one example, beam splitter 310 may receive condensed light beam 306 and divert a portion of the light beam (e.g., between 0.8% to 1.5% of the beam power) as second beam 306b while transmitting the remainder (e.g., between 99.2% to 97.5% of the beam power) as first beam 306a. In an exemplary embodiment, the optical fiber 308 is a 25 μm core and 0.26 NA multi-mode optical fiber with a 7 μm tolerance core diameter. In other embodiments, optical fibers with different diameters or sizes may be used.

Second beam 306b may be focused into the monitoring fiber 312. Monitoring fiber 312 may receive the second light beam 306b at a proximal end, and second light beam 306b may propagate within the monitoring fiber 306 and exit at a distal end of the monitoring fiber 312. Monitoring fiber 312 may have a length of several inches such that any light modes from the cladding of the monitoring fiber 312 are substantially eliminated. In certain embodiments, monitoring fiber 312 may have a smaller core diameter than that of the optical fiber 308. For example, one exemplary embodiment of a monitoring fiber 312 is a 4.3 μm core and 0.12 NA single-mode optical fiber. An optical sensor 314 may be provided at the distal end of the monitoring fiber 312 to detect the power or amount of the second beam 306a at the distal end.

In certain embodiments, it may be desirable to maintain a particular fixed arrangement between beam splitter 310, monitoring fiber 312, and the optical fiber 308 (which may be fixed by a surgical utility connector 108 housing optical fiber 308 being securely seated in a utility port 106). The particular fixed arrangement may be one in which first beam 306a and second beam 306b are parfocal except that the second beam 306b is folded. In other words, if folded second beam 306b were unfolded, the second beam 306b and the first beam 306a may coincide in space. Moreover, the particular fixed arrangement may be one in which the monitoring fiber 312 is located relative to second beam 306b in the same position as optical fiber 308 is located relative to first beam 306a. As a result, a coupling efficiency of the first beam 306a at the proximal end of optical fiber 308 may directly correspond to the coupling efficiency of the second beam 306b at the proximal end of monitoring fiber 306. Therefore, by monitoring the amount of the second beam 306b exiting the monitoring fiber 312 using optical sensor 314, the coupling efficiency of the first beam 306a at the optical fiber 308 may be determined.

Because the correspondence of the coupling efficiency of the second beam 306b at the proximal end of the monitoring fiber 306 and the coupling efficiency of the first beam 306a at the optical fiber 308 may be dependent upon the appropriate positioning of the proximal end of monitoring fiber 306, the proximal end of the monitoring fiber 306 may be housed in a ferrule 316 secured in a movable ferrule housing 318 that facilitates sub-micron alignment of the proximal end of the monitoring fiber 306 relative to the other components of ophthalmic endo-illumination system 206.

In certain embodiments, sub-micron alignment of the proximal end of the monitoring fiber 306 may be achieved by a set of displacement mechanisms 320 each operable to displace the moveable ferrule housing 318 is a particular direction. For example, a first displacement mechanisms 320a may facilitate movement of the moveable ferrule housing 318 in the X-direction, a second displacement mechanisms 320b may facilitate movement of the moveable ferrule housing 318 in the Y-direction, and a third displacement mechanisms 320c may facilitate movement of the moveable ferrule housing 318 in the Z-direction. Although a particular coordinate system has been applied in FIGS. 3A-3B for reference purposes, the present disclose contemplates movement of ferrule housing 318 relative to any suitable coordinate system.

Because each displacement mechanism 320 may be substantially the same except for the direction of movement of movable ferrule housing 318, a generic displacement mechanism 320 will be described for brevity. However, it should be understood that this description can be applied to any one of first displacement mechanism 320a, second displacement mechanism 320b, and third displacement mechanism 320c.

In certain embodiments, displacement mechanism 320 includes a screw actuator 322 having a sloped surface 324 contacting a motion transfer ball 326. The motion transfer ball 326 may contact a transfer spring 328 coupled to the moveable ferrule housing 318 in any suitable manner (e.g., using a retainer, as depicted). In general, movement of the screw actuator 322 may cause the motion transfer ball 326 to move along sloped surface 324, thereby causing displacement of the transfer spring 328 and resulting in displacement of the moveable ferrule housing 318.

In certain embodiments, displacement mechanism 320 may further comprise a linear screw 330 configured to rotate through one or more linear screw nuts 332 having fixed positions. As a result, rotation of linear screw 330 may be accompanied by linear movement of linear screw 330 in an axial direction. Additionally, linear screw 330 may be coupled to the screw actuator 322 comprising the sloped surface 324. Because screw actuator 322 is coupled to the linear screw 330, movement of linear screw 330 (e.g., by rotating linear screw 330 through linear screw nuts 332) may result in corresponding movement screw actuator 322. In certain embodiment, screw actuator 322 may be coupled to linear screw 330 such that linear screw 330 imparts linear movement (e.g., in a direction perpendicular to the displacement of moveable ferrule housing 318 by the displacement mechanism 320) but no rotational movement on screw actuator 322. Such movement of screw actuator 322 may cause the motion transfer ball 326 to move along sloped surface 324, thereby causing displacement of the transfer spring 328 and resulting in displacement of the moveable ferrule housing 318 (as discussed above).

The displacement of both motion transfer ball 326 and transfer spring 328 may be directly related to the pitch of linear screw 330 (pitch, P, may be calculated as P=1/N, where N is number of threads per unit length of linear screw 330). In other words, by selecting a pitch for motion transfer screw 330 (as well as other parameters of displacement mechanism 320, such as the slope of sloped surface 324), a desired amount of displacement of motion transfer ball 326 and transfer spring 328 may be achieved.

As one example, linear screw 330 may be a commercially available ¼-254 TPI (thread per inch) precision screw. Rotation of such a linear screw 330 by 90 degrees results linear travel of linear screw 330 by 0.025 mm (25 micron). Combining that amount of linear travel of linear screw 330 (and the screw actuator 322 coupled to linear screw 330) with a screw actuator 322 having a sloped surface 324 with an incline angle of 0.5 degrees, linear displacement of the motion transfer ball 326 contacting the sloped surface would be 0.22 micron. As another example, if the same ¼-254 linear screw 330 is rotated by 10 degrees, linear displacement of the motion transfer ball 326 contacting the 0.5 degree sloped surface would be 0.024 micron.

In certain embodiments, displacement of the moveable ferrule housing 318 (as a result of the above-discussed linear displacement of the motion transfer ball 326) may be opposed by one or more support springs 334. Transfer spring 328 and support spring(s) 334 may each comprise any suitable compression springs (e.g., linear coil compression springs, linear flexure compression springs, or any other suitable compression springs) having spring constants, k. In certain embodiments, both transfer spring 328 and a corresponding support spring 334 may be decompressed and may be preloaded to a certain load factor such that the movable ferrule housing 318 is stable and has no free play and no backlash. In other words, one or more support springs 334 opposing displacement of the moveable ferrule housing 318 (as imparted via transfer spring 328) may provide for increases stability and shock resistance for movable ferrule housing 318.

In certain embodiments, transfer spring 328 and the corresponding support spring 334 may have different spring constants $k_1$ and $k_2$, respectively. As a result, transfer spring 328 and support spring 334 may have different displacements at the same preload force. From Hooke's law, linear displacement of a spring can be calculated using the formula $x=(1/k) F$ [N/m] and spring constant can be calculated using the formula $k=F/x$ [N/m]. Therefore, the travel of both transfer spring 328 and support spring 334 can be calculated if either force or displacement is known, and vice versa. Accordingly, if it is assumed that at a predetermined amount of rotation of linear screw 330 results in displacement (via motion transfer ball 326) of transfer spring 328 an amount $x_1$, that transfer spring 328 has a spring constant $k_1$, and that support spring 334 has a spring constant $k_2$, then a resulting displacement $x_2$ of support spring 334 (which will correspond to the displacement of moveable ferrule housing 318) can be calculated. In other words, by selecting spring constants for transfer spring 328 and support spring 334 (as well as other parameters of displacement mechanism 320, such as the slope of sloped surface 324 and the pitch of linear screw 330, as discussed above), a desired amount of displacement of moveable ferrule housing 318 for a given rotation of linear screw 330 may be achieved. Although the above-described example assumes only a single support spring 334 corresponding to a single transfer spring 328, the same analysis would apply to any suitable number of support springs 334 and transfer springs 328.

In certain embodiments, moveable ferrule housing 318 may be supported by one or more support balls 336 and one or more contact balls 338. Support balls 336 and contact balls 338 (like motion transfer balls 326, discussed above) may be any suitable size and constructed of any suitable material. In response to a displacement force supplied by a displacement mechanism 320 in the manner discussed above, moveable ferrule housing 318 may roll across the surface of support balls 336, thereby facilitating movement of moveable ferrule housing 318 with little resistance due to friction. Contact balls 338 may be distributed about the perimeter of moveable ferrule housing 318 and may contact corresponding contact plates 340. Contact balls 338 and contact plates 340 may allow even distribution of the force applied to moveable ferrule housing 318 by support springs 334 regardless of movement of moveable ferrule housing 318. Although a particular number and arrangement of support balls 336, contact balls 338, and contact plates 340 is depicted, the present disclosure contemplates any suitable number and arrangement of support balls 336, contact balls 338, and contact plates 340.

In certain embodiments, rotation of a linear screw 330 of a displacement mechanism 320 may be achieved manually using an actuation key. For example, a user (e.g., a person charged with sub-micron alignment of the proximal end of the monitoring fiber 306) may insert an actuation key into a corresponding location of each linear screw 330a, 330b, and 330c, and, by manually turning linear screws 330, move moveable ferrule housing 318 such that proper alignment of the proximal end of the monitoring fiber 306 is achieved. Alternatively, each linear screw 330a, 330b, and 330c may have a corresponding drive motor (e.g., an electric motor having micro-stepping capability and a gearbox) such that automated movement of moveable ferrule housing 318 may be achieved. In such an embodiment, alignment of the proximal end of the monitoring fiber 306 may be automated (e.g., using the feedback provided by optical sensor 314).

Figure 4B:
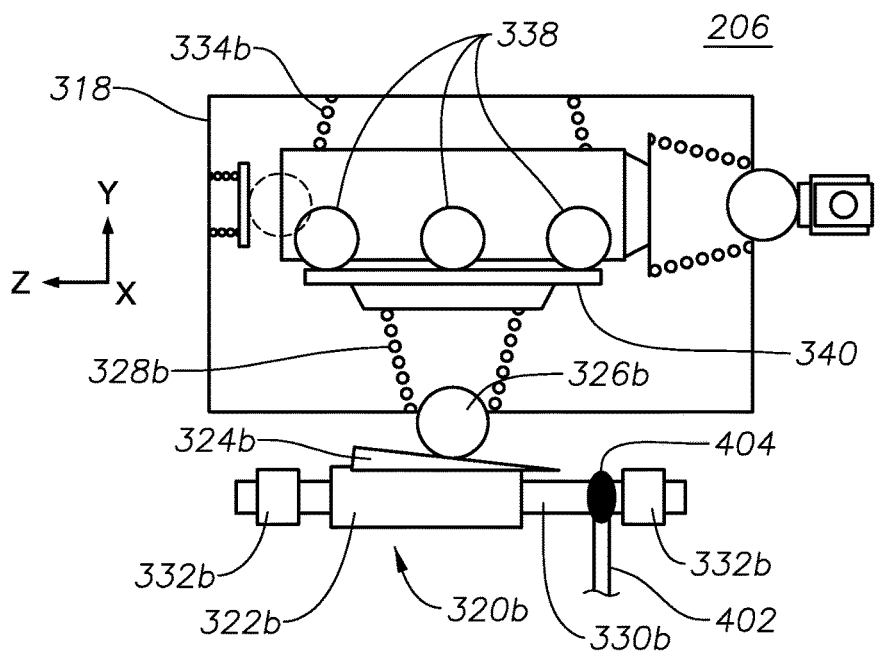
FIGS. 4A-4B illustrate a schematic diagram of the exemplary ophthalmic endo-illumination system of FIG. 2 in which the position of a moveable ferrule may be fixed once proper alignment of a monitoring fiber is achieved, according to certain embodiments of the present disclosure.
Figure 4A:
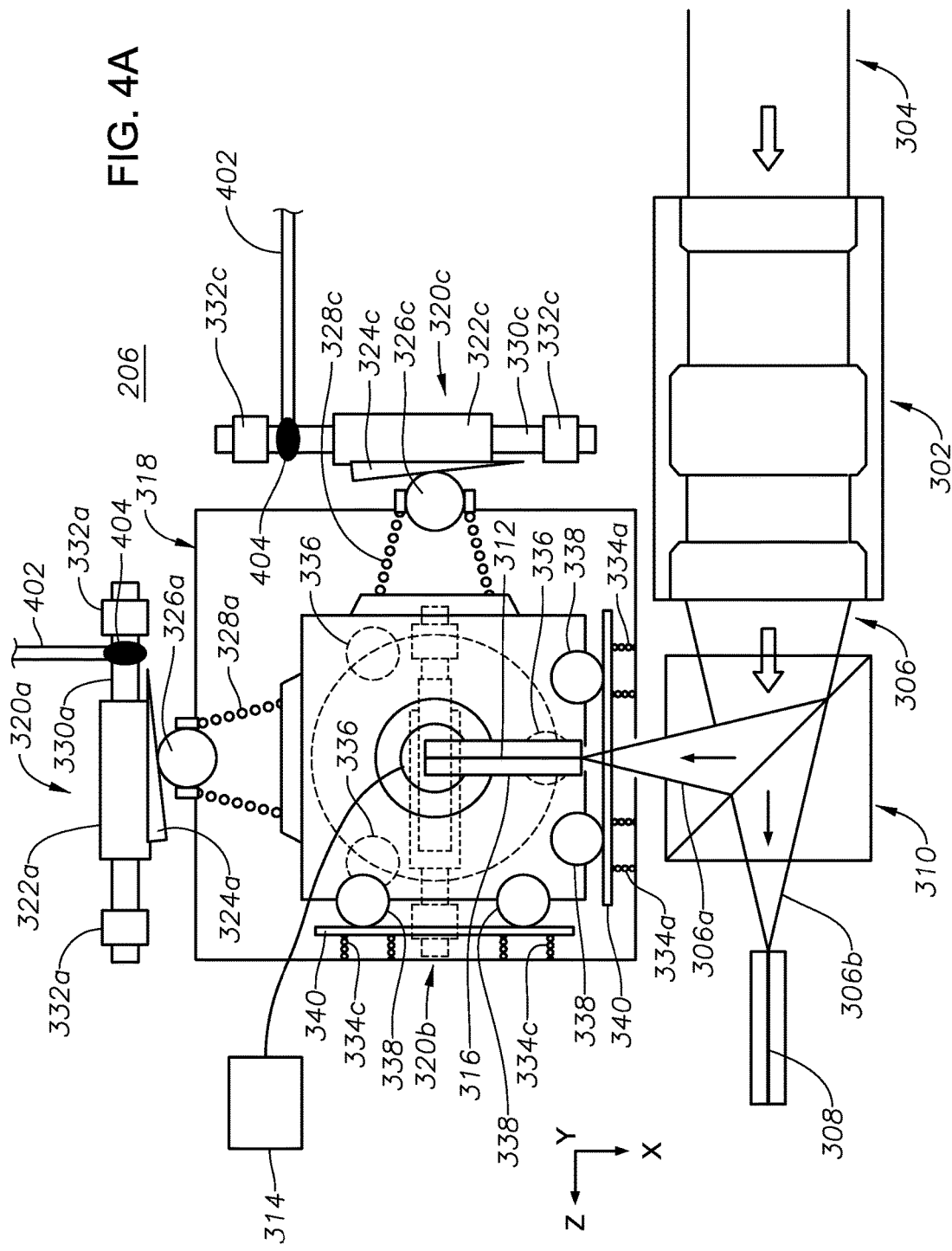

Once proper alignment of the proximal end of the monitoring fiber 306 is achieved using the above discussed alignment system, it may be desirable to fix the position of the proximal end of the monitoring fiber 306. FIGS. 4A-4B illustrate a schematic diagram of the exemplary ophthalmic endo-illumination system 206 in which the position of moveable ferrule 318 may be fixed once proper alignment of monitoring fiber 312 is achieved, according to certain embodiments of the present disclosure. In particular, channels 402 may be formed the housing of ophthalmic endo-illumination system 206 such that epoxy 404 may be applied to linear screws 330 to prevent movement of linear screws 330, thereby preventing movement of moveable ferrule housing 318. Advantageously, fixing the position of moveable ferrule housing 318 by applying epoxy 404 to linear screws 330 may allow for thermal expansion of epoxy 404 without resulting in movement of moveable ferrule housing 318. Although channels 402 are depicted as being formed at particular locations in the housing such that epoxy 404 is applied to particular portions of linear screws 330, the present disclosure contemplates channels 402 being formed at any suitable locations in the housing such that epoxy 404 may be applied to any suitable portions of linear screws 330.

Alternatively, in embodiments in which each linear screw 330a, 330b, and 330c has a corresponding drive motor, movement of moveable ferrule housing 318 may be prevented by locking the drive motors. Advantageously, this may allow for alignment of the proximal end of the monitoring fiber 306 at varying point in time.

Although particular mechanisms for preventing movement of moveable ferrule housing 318 once alignment of the monitoring fiber 306 is achieved are described, the present disclosure contemplates any suitable mechanism for preventing movement of moveable ferrule housing 318 once alignment of the proximal end of the monitoring fiber 306 is achieved. As just one example, thread-locking features, such as plastic screw tips (nylon screw tips), may be incorporated into linear screws 330.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An ophthalmic endo-illumination system, comprising:
a light source configured to produce a light beam;
a condenser configured to provide at least a portion of the light beam to a fiber port configured to couple the at least a portion of the light beam to an optical fiber of an illumination probe;
a beam splitter disposed between the fiber port and the condenser, the beam splitter configured to receive the light beam from the condenser and split the light beam into a first beam a second beam, the first beam being provided to the fiber port and the second beam being coupled to a monitoring fiber; and
an alignment system for aligning the monitoring fiber with the second beam, the alignment system comprising:
a moveable ferrule housing having the monitoring fiber secured therein; and
a first displacement mechanism for displacing the moveable ferrule housing in a first direction, the first displacement mechanism comprising:
a transfer spring coupled to the moveable ferrule housing; and
a screw actuator having a sloped surface contacting a motion transfer ball such that movement of the screw actuator causes the motion transfer ball to move along the sloped surface, the motion transfer ball contacting the transfer spring such that movement of the motion transfer ball along the sloped surface causes a displacement of the transfer spring, thereby displacing the moveable ferrule housing in the first direction.

2. The ophthalmic endo-illumination system of claim 1, wherein the alignment system further comprises a first one or more support springs coupled to the to the moveable ferrule housing and opposing displacement of the moveable ferrule housing in the first direction.

3. The ophthalmic endo-illumination system of claim 1, wherein the alignment system further comprises a second displacement mechanism for displacing the moveable ferrule housing in a second direction, the second displacement mechanism comprising:
a transfer spring coupled to the moveable ferrule housing; and
a screw actuator having a sloped surface contacting a motion transfer ball such that movement of the screw actuator causes the motion transfer ball to move along the sloped surface, the motion transfer ball contacting the motion transfer spring such that movement of the motion transfer ball along the sloped surface causes a displacement of the motion transfer spring, thereby displacing the moveable ferrule housing in the second direction.

4. The ophthalmic endo-illumination system of claim 3, wherein the alignment system further comprises a second one or more support springs coupled to the to the moveable ferrule housing and opposing displacement of the moveable ferrule housing in the second direction.

5. The ophthalmic endo-illumination system of claim 3, wherein the alignment system further comprises a third displacement mechanism for displacing the moveable ferrule housing in a third direction, the second displacement mechanism comprising:
a transfer spring coupled to the moveable ferrule housing; and
a screw actuator having a sloped surface contacting a motion transfer ball such that movement of the screw actuator causes the motion transfer ball to move along the sloped surface, the motion transfer ball contacting the motion transfer spring such that movement of the motion transfer ball along the sloped surface causes a displacement of the motion transfer spring, thereby displacing the moveable ferrule housing in the third direction.

6. The ophthalmic endo-illumination system of claim 5, wherein the alignment system further comprises a third one or more support springs coupled to the to the moveable ferrule housing and opposing displacement of the moveable ferrule housing in the third direction.

7. The ophthalmic endo-illumination system of claim 5, wherein the alignment system further comprises:
a first actuation key facilitating manual movement of the screw actuator of the first displacement mechanism;
a second actuation key facilitating manual movement of the screw actuator of the second displacement mechanism; and
a third actuation key facilitating manual movement of the screw actuator of the third displacement mechanism.

8. The ophthalmic endo-illumination system of claim 5, wherein the alignment system further comprises:
a first drive motor facilitating movement of the screw actuator of the first displacement mechanism;
a second drive motor facilitating movement of the screw actuator of the second displacement mechanism; and a third drive motor facilitating movement of the screw actuator of the third displacement mechanism.

9. The ophthalmic endo-illumination system of claim 5, wherein the alignment system further comprises:
   a first cavity corresponding to the first displacement mechanism, the first cavity facilitating fixation of the first displacement mechanism to prevent displacement of the moveable ferrule housing in the first direction;
   a second cavity corresponding to the second displacement mechanism, the first cavity facilitating fixation of the first displacement mechanism to prevent displacement of the moveable ferrule housing in the second direction; and
   a third cavity corresponding to the third displacement mechanism, the first cavity facilitating fixation of the first displacement mechanism to prevent displacement of the moveable ferrule housing in the third direction.

10. The ophthalmic endo-illumination system of claim 9, wherein the first, second, and third cavities are each configured to receive an epoxy, the epoxy, when cured in the first, second, and third cavities, preventing movement of the screw actuators of the first, second, and third displacement mechanisms, thereby preventing displacement of the moveable ferrule housing in the first, second, and third directions.

11. An alignment system for aligning a monitoring fiber with a corresponding light beam, comprising:
   a moveable ferrule housing having the monitoring fiber secured therein; and
   a first displacement mechanism for displacing the moveable ferrule housing in a first direction, the first displacement mechanism comprising:
      a transfer spring coupled to the moveable ferrule housing; and
      a screw actuator having a sloped surface contacting a motion transfer ball such that movement of the screw actuator causes the motion transfer ball to move along the sloped surface, the motion transfer ball contacting the transfer spring such that movement of the motion transfer ball along the sloped surface causes a displacement of the transfer spring, thereby displacing the moveable ferrule housing in the first direction.

12. The ophthalmic endo-illumination system of claim 11, wherein the alignment system further comprises a first one or more support springs coupled to the to the moveable ferrule housing and opposing displacement of the moveable ferrule housing in the first direction.

13. The alignment system of claim 11, wherein the alignment system further comprises a second displacement mechanism for displacing the moveable ferrule housing in a second direction, the second displacement mechanism comprising:
   a transfer spring coupled to the moveable ferrule housing; and
   a screw actuator having a sloped surface contacting a motion transfer ball such that movement of the screw actuator causes the motion transfer ball to move along the sloped surface, the motion transfer ball contacting the motion transfer spring such that movement of the motion transfer ball along the sloped surface causes a displacement of the motion transfer spring, thereby displacing the moveable ferrule housing in the second direction.

14. The alignment system of claim 13, wherein the alignment system further comprises a second one or more support springs coupled to the to the moveable ferrule housing and opposing displacement of the moveable ferrule housing in the second direction.

15. The alignment system of claim 13, wherein the alignment system further comprises a third displacement mechanism for displacing the moveable ferrule housing in a third direction, the second displacement mechanism comprising:
   a transfer spring coupled to the moveable ferrule housing; and
   a screw actuator having a sloped surface contacting a motion transfer ball such that movement of the screw actuator causes the motion transfer ball to move along the sloped surface, the motion transfer ball contacting the motion transfer spring such that movement of the motion transfer ball along the sloped surface causes a displacement of the motion transfer spring, thereby displacing the moveable ferrule housing in the third direction.

16. The alignment system of claim 15, wherein the alignment system further comprises a third one or more support springs coupled to the to the moveable ferrule housing and opposing displacement of the moveable ferrule housing in the third direction.

17. The alignment system of claim 15, wherein the alignment system further comprises:
   a first actuation key facilitating manual movement of the screw actuator of the first displacement mechanism;
   a second actuation key facilitating manual movement of the screw actuator of the second displacement mechanism; and
   a third actuation key facilitating manual movement of the screw actuator of the third displacement mechanism.

18. The alignment system of claim 15, wherein the alignment system further comprises:
   a first drive motor facilitating movement of the screw actuator of the first displacement mechanism;
   a second drive motor facilitating movement of the screw actuator of the second displacement mechanism; and
   a third drive motor facilitating movement of the screw actuator of the third displacement mechanism.

19. The alignment system of claim 15, wherein the alignment system further comprises:
   a first cavity corresponding to the first displacement mechanism, the first cavity facilitating fixation of the first displacement mechanism to prevent displacement of the moveable ferrule housing in the first direction;
   a second cavity corresponding to the second displacement mechanism, the first cavity facilitating fixation of the first displacement mechanism to prevent displacement of the moveable ferrule housing in the second direction; and
   a third cavity corresponding to the third displacement mechanism, the first cavity facilitating fixation of the first displacement mechanism to prevent displacement of the moveable ferrule housing in the third direction.

20. The alignment system of claim 19, wherein the first, second, and third cavities are each configured to receive an epoxy, the epoxy, when cured in the first, second, and third cavities, preventing movement of the screw actuators of the first, second, and third displacement mechanisms, thereby preventing displacement of the moveable ferrule housing in the first, second, and third directions.

* * * * *